(12) United States Patent
Boveja

(10) Patent No.: US 6,449,512 B1
(45) Date of Patent: Sep. 10, 2002

(54) APPARATUS AND METHOD FOR TREATMENT OF UROLOGICAL DISORDERS USING PROGRAMMERLESS IMPLANTABLE PULSE GENERATOR SYSTEM

(76) Inventor: Birinder R. Boveja, P.O. Box 210092, Milwaukee, WI (US) 53221

( * ) Notice: Subject to any disclaimer, the term of this patent is extended or adjusted under 35 U.S.C. 154(b) by 0 days.

(21) Appl. No.: 09/942,321

(22) Filed: Aug. 29, 2001

(51) Int. Cl.[7] ................................................. A61N 1/08
(52) U.S. Cl. ............................ 607/41; 607/30; 600/30
(58) Field of Search ............................ 607/40–41, 30; 600/29, 30

(56) References Cited

U.S. PATENT DOCUMENTS

| | | |
|---|---|---|
| 4,387,719 A | 6/1983 | Plevnik et al. |
| 4,884,575 A | 12/1989 | Sanders |
| 5,304,206 A | 4/1994 | Baker et al. |
| 5,769,877 A * | 6/1998 | Barreras, Sr. |

OTHER PUBLICATIONS

"A Hand–held Controller Dedicated to Implantable Stimulators" Simon Robin & Mohamad Swan, 1996.*
Department of Electrical & Computer Engineering École Polytechnique de Montréal.*
Low–Power CMOS Implantable Nerve Signal Analog Processing Circuit, 1999.*
Adnan Harb & Mohamad Swan École Polytechnique de Montréal.*

* cited by examiner

Primary Examiner—Mark Bockelman

(57) ABSTRACT

System and method of neuromodulation therapy for urinary incontinence disorders comprises a lead to selectively stimulate the sacral plexus and an implantable pulse generator for providing the appropriate pulses. The implantable pulse generator having prepackaged/predetermined programs stored in the memory of the pulse generator, and means for accessing these with an external magnet. The pulse generator adapted to selectively activate predetermined programs with the external magnet, thereby eliminating the need for an external programmer. The elimination of the external programmer resulting in significant cost reduction with essentially the same functionality.

11 Claims, 11 Drawing Sheets

APPARATUS AND METHOD FOR TREATMENT OF UROLOGICAL DISORDERS USING PROGRAMMERLESS IMPLANTABLE PULSE GENERATOR SYSTEM

FIELD OF THE INVENTION

The present invention relates generally to implantable medical prostheses, more specifically, implantable pulse generator for treating or controlling urological disorders using pulsed sacral nerve stimulation.

The method and apparatus disclosed herein may also be appropriate for the treatment of other conditions, as disclosed in co-pending application filed on Aug. 29, 2001 entitled APPARATUS AND METHOD FOR TREATMENT OF NEUROLOGICAL AND NEUROPSYCHIATRIC DISORDERS USING PROGRAMMERLESS IMPLANTABLE PULSE GENERATOR SYSTEM.

BACKGROUND OF THE INVENTION

Sacral nerve electrical neuromodulation has shown beneficial medical effects for urinary incontinence and a broad group of urological disorders. This patent is directed to a system of implantable lead and pulse generator which is programmerless, and the pulse generator being controlled by only an external magnet.

Implanted pulse generator (IPG) systems for neuromodulation generally consist of an implantable lead, an implantable pulse generator, and an external programmer for non-invasively programming the parameters of the IPG.

The programmer generally is a microprocessor-based device, which provides a series of encoded signals to the implanted pulse generator by means of a programming head which transmits radio-frequency (RF) encoded signals to pulse generator according to the telemetry system laid out in that system. Such a system requires an antenna which is connected to input/output circuit for purposes of uplink/downlink telemetry through an RF telemetry circuit.

A built-in antenna enables communication between the implanted pulse generator and the external electronics (including both programming and monitoring devices) to permit the device to receive programming signals for parameter changes, and to transmit telemetry information, from and to the programming wand. Once the system is programmed, it operates continuously at the programmed settings until they are reprogrammed (by the attending physician) by means of the external computer and the programming wand.

In such a system any programming methodology may be employed so long as the desired information can be conveyed between the pulse generator and the external programmer.

Generally, neurostimulator systems for urinary incontinence and other urological disorders work quite well, except that their manufacturing costs and corresponding selling price tends to be high and places a burden on the health care system. A significant part of the cost is attributed to the programmability of the implanted device, as well as, the computer-based programmer itself.

Historically, implantable neurostimulator technology evolved based significantly on the existing cardiac pacemaker technology. Both are essentially electrical pulse generators. However, there is one significant difference, which is, for a cardiac pacemaker to function properly it needs to sense the electrical activity of the stimulating tissue. Therefore, in a cardiac pacemaker an external programmer is an integral part of the system to program the sensitivity. A system for neuromodulation is not dependent upon sensing from the stimulating tissue such as the nerve, before providing electrical pulses.

Thus, by incorporating a limited number of predetermined/prepackaged programs into the implantable pulse generator, a significant manufacturing and development cost reduction for the system can be achieved, with very little loss of functionality.

Urinary Urge Incontinance

In considering the background of urinary urge incontinence, FIG. 1 shows a sagittal section of the human female pelvis showing the bladder 10 and urethra 13 in relation to other anatomic structures. Urinary continence requires a relaxed bladder during the collecting phase and permanent closure of the urethra, whereas at micturition (urination), an intravesical pressure above the opening pressure of the simultaneously relaxing urethra has to be generated. These functions of the bladder and urethra are centrally coordinated and non-separable. At bladder filling, the sensation of urge is mediated by slowly adapting mechanoreceptors in the bladder wall and the same receptors provide the triggering signal for micturition and the main driving force for a sustained micturition contraction. The mechanoreceptors are, technically speaking, tension receptors. It has been found that they respond equally well to tension increases induced passively by bladder filling and those induced actively by a detrusor contraction. These receptors have high dynamic sensitivity and are easily activated by external pressure transients, as may occur during coughing or tapping of the abdominal wall. Their faithful response to active changes in bladder pressure is well illustrated.

When sufficiently activated, the mechanorecptors trigger a coordinated micturition reflex via a center in the upper pons 88, as depicted schematically in FIG. 2. The reflex detrusor 92 (muscle in the wall of the urinary bladder) contraction generates an increased bladder pressure and an even stronger activation of the mechanoreceptors. Their activity in turn reinforces the pelvic motor output to the bladder, which leads to a further increase in pressure and more receptor activation and so on. In this way, the detrusor contraction is to a large extent self generating once initiated. Such a control mechanism usually is referred to as a positive feedback, and it may explain the typical all-or-nothing behavior of the parasympathetic motor output to the bladder. Once urine enters the urethra, the contraction is further enhanced by reflex excitation from urethral receptors. Quantitatively, the bladder receptors are most important.

A great advantage of the positive feedback system is that it ascertains a complete emptying of the bladder during micturition. As long as there is any fluid left in the lumen, the intravesical pressure will be maintained above the threshold for the mechanoreceptors and thus provide a continuous driving force for the detrusor. A drawback with this system is that it can easily become unstable. Any stimulus that elicits a small burst of impulses in mechanoreceptor afferents may trigger a full-blown micturition reflex. To prevent this from happening during the filling phase, the neuronal system controlling the bladder is equipped with several safety devices both at the spinal and supraspinal levels.

The best-known spinal mechanism is the reflex control of the striated urethral sphincter 90, which increases its activity in response to bladder mechanoreceptor activation during filling. An analogous mechanism is Edvardsen's reflex, which involves machanoreceptor activation of inhibitory sympathetic neurons to the bladder. The sympathetic efferents have a dual inhibitory effect, acting both at the post-ganglionic neurons in the vesical ganglia and directly on the detrusor muscle of the bladder 92. The sphincter and sympathetic reflexes are automatically turned off at the spinal cord level during a normal micturation. At the supraspinal level, there are inhibitory connections from the cerebral cortex and hypothalamus to the pontine micturition center. The pathways are involved in the voluntary control of continence. Other inhibitory systems seem to originate from the pontine and medullary parts of the brainstem with at least partly descending connections.

Bladder over-activity and urinary urge incontinence may result from an imbalance between the excitatory positive feedback system of the bladder 10 and inhibitory control systems causing a hyperexcitable voiding reflex. Such an imbalance may occur after macroscopic lesions at many sites in the nervous system or after minor functional disturbances of the excitatory or inhibitory circuits. Urge incontinence due to detrusor instability seldom disappears spontaneoulsly. The symptomatic pattern also usually is consistent over long periods.

Based on clinical experience, subtypes of urinary incontinance include, Phasic detrusor instability and uninhibited overactive bladder. Phasic detrusor instability is characterized by normal or increased bladder sensation, phasic bladder contractions occurring spontaneously during bladder filling or on provocation, such as by rapid filling, coughing, or jumping. This condition results from a minor imbalance between the bladder's positive-feedback system and the spinal inhibitory mechanisms. Uninhibited overactive bladder is characterized by loss of voluntary control of micturition and impairment of bladder sensation. The first sensation of filling is experienced at a normal or lowered volume and is almost immediately followed by involuntary micturition. The patient does not experience a desire to void until she/he is already voiding with a sustained detrusor contraction and a concomitant relaxation of the urethra, i.e., a well-coordinated micturition reflex. At this stage, she/he is unable to interrupt micturition voluntarily. The sensory disturbance of these subjects is not in the periphery, at the level of bladder mechanoreceptors, as the micturition reflex occurs at normal or even small bladder volumes. More likely, the suprapontine sensory projection to the cortex is affected. Such a site is consistent with the coordinated micturition and the lack of voluntary control. The uninhibited overactive bladder is present in neurogenic dysfunction.

Since bladder over-activity results from defective central inhibition, it seems logical to improve the situation by reinforcing some other inhibitory system. Patients with stress and urge incontinence are difficult to treat adequately. Successful therapy of the urge component does not influence the stress incontinence. While an operation for stress incontinence sometimes results in deterioration of urgency. Electro stimulation is a logical alternative in mixed stress and urge incontinence, since the method improves urethral closure as well as bladder control. Drug treatment often is insufficient and, even when effective, does not lead to restoration of a normal micturition pattern.

Neuromodulation is a technique that uses electrical stimulation of the sacral nerves, (a general diagram of spinal cord and sacral nerves 85 is shown in FIG. 3). The aim of this treatment modality is to achieve detrusor 92 inhibition by chronic electrical stimulation of afferent somatic sacral nerve fibers 85 via implanted electrodes connected to a subcutaneously placed pulse generator.

The rationale of this treatment modality is based on the existence of spinal inhibitory systems that are capable of interrupting a detrusor 92 contraction. Inhibition can be achieved by electrical stimulation of afferent anorectal branches of the pelvic nerve, afferent sensory fibers in the pudendal nerve and muscle afferents from the limbs. Most of these branches and fibers reach the spinal cord via the dorsal roots of the sacral nerves 85. Of the sacral nerve roots the S3 and S4 roots are the most practical for use in chronic electrical stimulation.

In neuromodulation, the entire innervation system should be intact. As shown schematically in FIG. 4, the procedure consists of placing electrodes 61,62 in one of the sacral foraman as close to the pelvic plexus and pudendal nerve as possible and connecting the lead 40 with a pulse generator 70. The hypothesis behind neuromodulation of the sacral roots (sensory and motor) is to correct, by the use of regulating electrical impulses, the dys-synergic activities of the cholinergic, adrenergic, and motor reflex pathways that initiate vesical storage and micturition. Although some theories have been developed that explain the effects of neuromodulation, most of the results are based on empiric findings in human studies. Some animal experiments and electrophysiologic studies in humans show there is a spinal inhibitory action through the afferent branches of the pelvic and pudendal nerves. It is not clear whether neuromodulation primarily influences the micturiction center located near the thalamus in the brain. Some maintain that there is a direct correction of the dys-synergis of the pelvic floor (pudendal nerve) by influencing the abnormal contractility of the pelvic floor.

A neurophysiological explanation for the effectiveness of this treatment modality in detrusor instability is based on animal experiments and electrophysiological studies in humans. Electrical stimulation for the treatment of urinary incontinence has evolved over the past 40 years. The mechanism of action of electrical stimulation was investigated initially in animal models. Over 100 years ago, Griffiths demonstrated relaxation of a contracted detrusor during stimulation of the proximal pudendal nerve in the cat model and further work clarified the role of pudendal afferents in relation of the detrusor. Spinal inhibitory systems capable of interrupting a detrusor contraction can be activated by electrical stimulation of afferent anorectal branhes of the pelvic nerve, afferent sensory fibers in the pudendal nerve and muscle afferents from the limbs. The effectiveness of neuromodulation in humans has been objectively demonstrated by urodynamic improvement, especially in light of the fact that such effects have not been noted in drug trials.

Neuromodulation also acts on neural reflexes but does so internally by stimulation of the sacral nerves 85. Sacral nerve 85 stimulation is based on research dedicated to the understanding of the voiding reflex as well as the role and influence of the sacral nerves 85 on voiding behavior. This research led to the development of a technique to modulate dysfunctional voiding behavior through sacral nerve stimulation. It is thought that sacral nerve stimulation induces reflex mediated inhibitory effects on the detrusor through afferent and/or efferent stimulation of the sacral nerves 85.

Even though the precise mechanism of action of electrical stimulation in humans is not fully understood, it has been shown that sensory input traveling through the pudendal nerve can inhibit detrusor activity in humans. Most experts believe that non-implanted electrical stimulation works by stimulating the pudendal nerve afferents, with the efferent outflow causing contraction of the striated pelvic musculature. There is also inhibition of inappropriate detrusor activity, though the afferent mechanism has yet to be clarified. There is consensus that the striated musculature action is able to provide detrusor inhibiton in this setting, though data supporting this hypotheses are lacking.

In summary, the rationale for neuromodulation in the management of such patients is the observation that stimulation of the sacral nerves via electrical stimulation can inhibit inappropriate neural reflex behavior.

U.S. Pat. No. 4,387,719 (Plevnik) is directed to control circuitry of a therapeutic stimulator for urinary incontinence, whereby the urethral sphincter is stimulated and at the same time a reflected inhibition of the urinary bladder is caused. In the Plevnik '719 patent stimulation pulses are generated, and may be automatically interrupted after predetermined periods of time.

U.S. Pat. No. 4,884,575 (Sanders) is directed to a cardiac pacemaker adapted to generate a first pacing rate, and to selectively increase the rate to higher exercise rate which can be triggered with a time delay. In the Sanders patent, their is no suggestion to have a limited number of prepackaged/predetermined programs built into the pacemaker, and to selectively activate them with only a magnet. In a cardiac pacemaker, an external programmer is essential to adjust the sensitivity of the pacemaker, such that the pacemaker does not compete with the intrinsic rhythm of the heart.

In contrast, in the current patent application for neuromodulation of the sacral nerve for controlling urinary incontinence, there is no sensing involved from the stimulation tissue, i.e. the sacral nerve plexus. Therefore, all of the stimulation programs containing the different electrical stimulation parameters, can be built-in, and which can be selectively activated with a magnet. This eliminates the need for an external programmer.

U.S. Pat. No. 5,304,206 (Baker et al) is directed to techniques and apparatus for activating implanted neurostimulators. In the Baker patent, the implanted device communicates with a programmer and/or monitor external to the patient's body by means of asynchronous serial communication, to control and indicate device states. Further, the patient can adjust the implanted generator by finger tapping, whereby a piezoelectric sensor is activated. There is no suggestion in the Baker patent to simplify the implant by having prepackaged/predetermined programs in the implant, and eliminating the programmer.

SUMMARY OF THE INVENTION

A drawback of the prior art neuromodulation system is that it adds significant cost to the system. In the system of the current invention, high value is provided by eliminating the development of a computer based programmer to control the implanted pulse generator.

Accordingly, an apparatus and method of this invention comprises an implantable pulse generator and lead system which is adapted to provide pulsed electrical stimulation to sacral nerve plexus. The pulse generator comprises a limited number of predetermined/prepackaged program built into the implanted pulse generator. These predetermined programs can be accessed by an external magnet, thus eliminating the need for an expensive computer based external programmer.

BRIEF DESCRIPTION OF THE DRAWING

For the purpose of illustrating the invention, there are shown in accompanying drawing forms which are presently preferred, it being understood that the invention is not intended to be limited to the precise arrangement and instrumentatlities shown.

DESCRIPTION OF THE INVENTION

The following description is of the current embodiment for carrying out the invention. This description is not to be taken in a limiting sense, but is made merely for the purpose of describing the general principles of the invention. The scope of the invention should be determined with reference to the claims.

Figure 1:
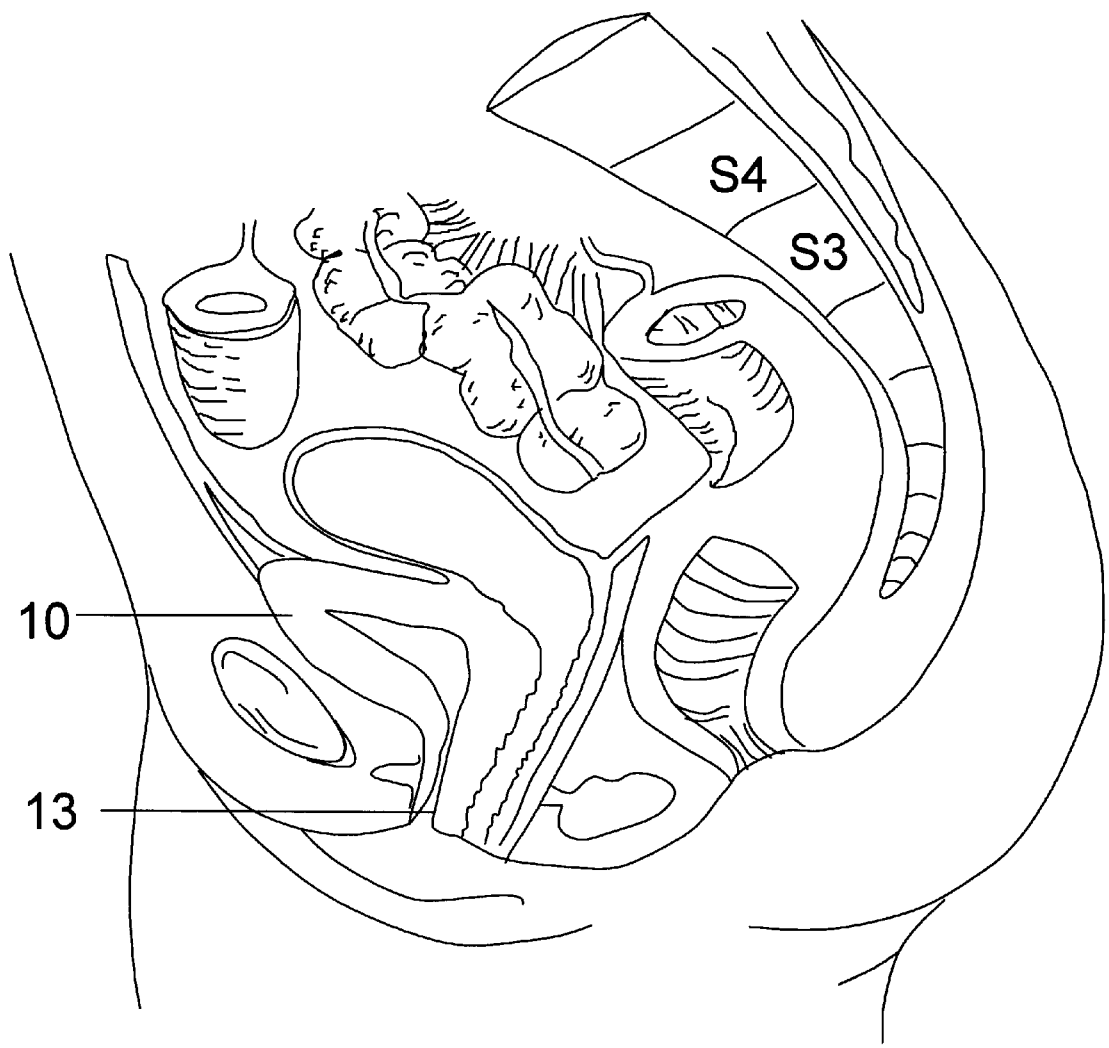
FIG. 1 shows a diagram of the sagittal section of the female pelvis, showing the relationship between various anatomic structures.
Figure 2:
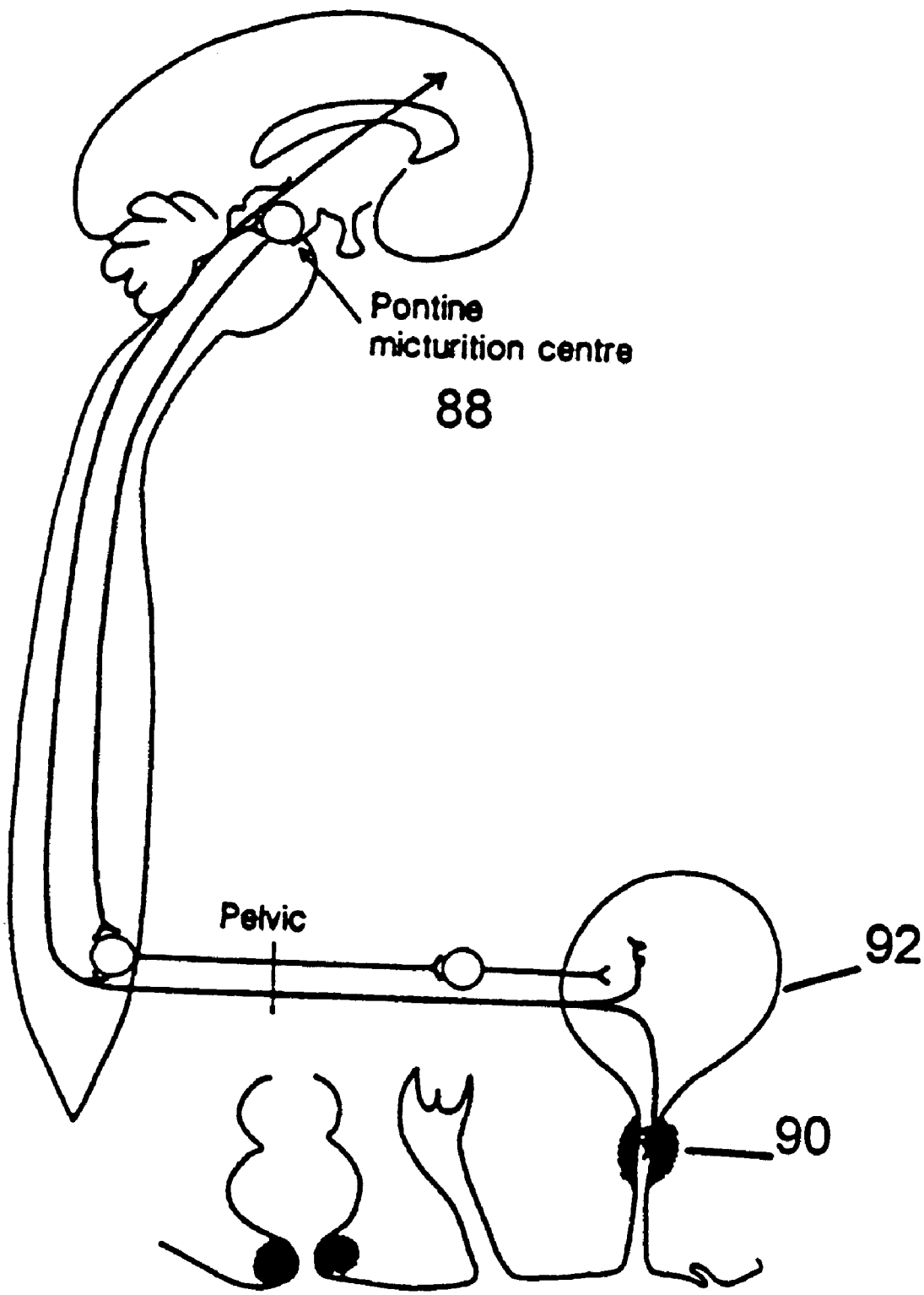
FIG. 2 is a schematic diagram showing physiological control of micturition.
Figure 3:
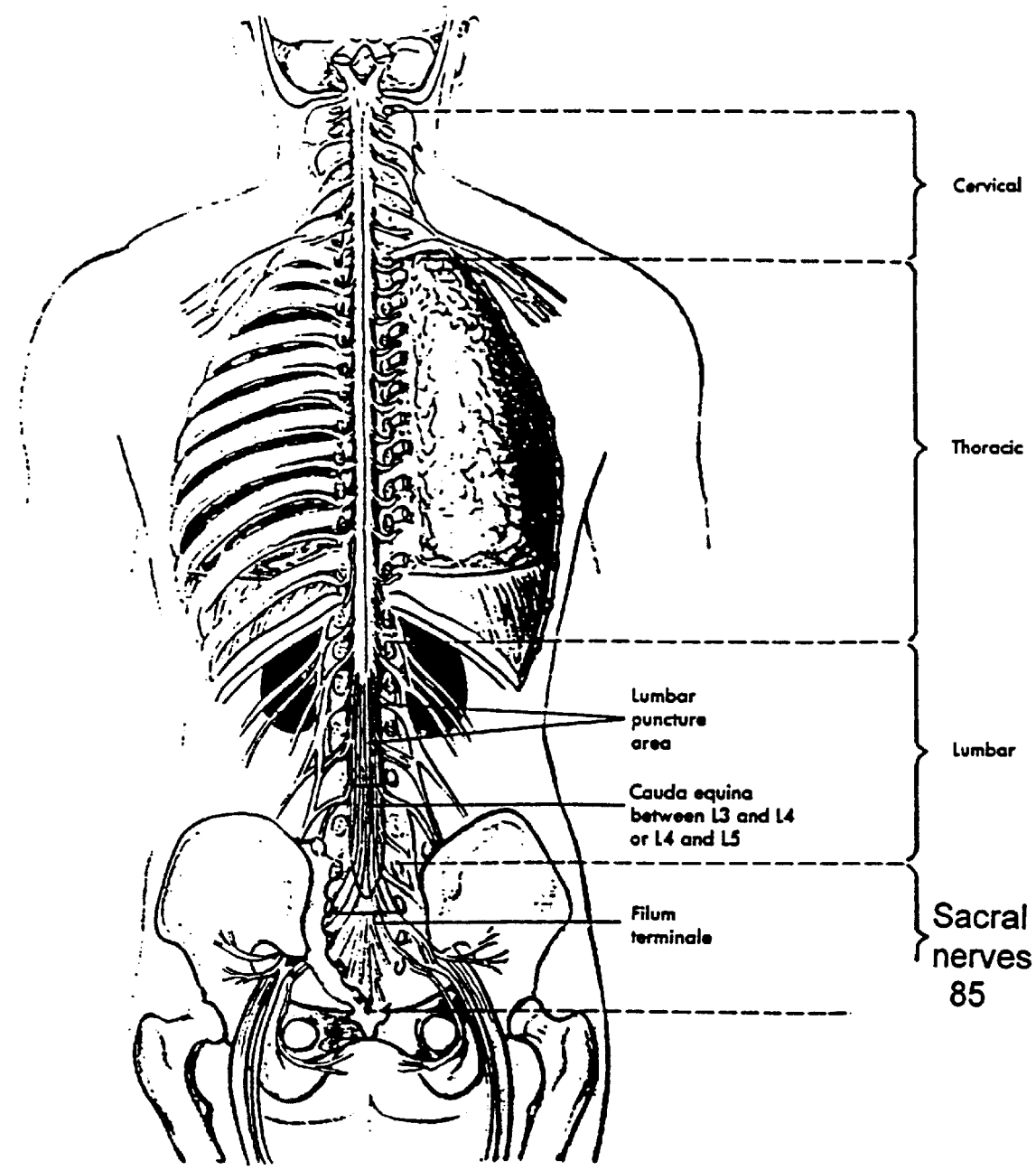
FIG. 3 is a diagram showing anatomic relationships of spinal nerves and sacral plexus.
Figure 4:
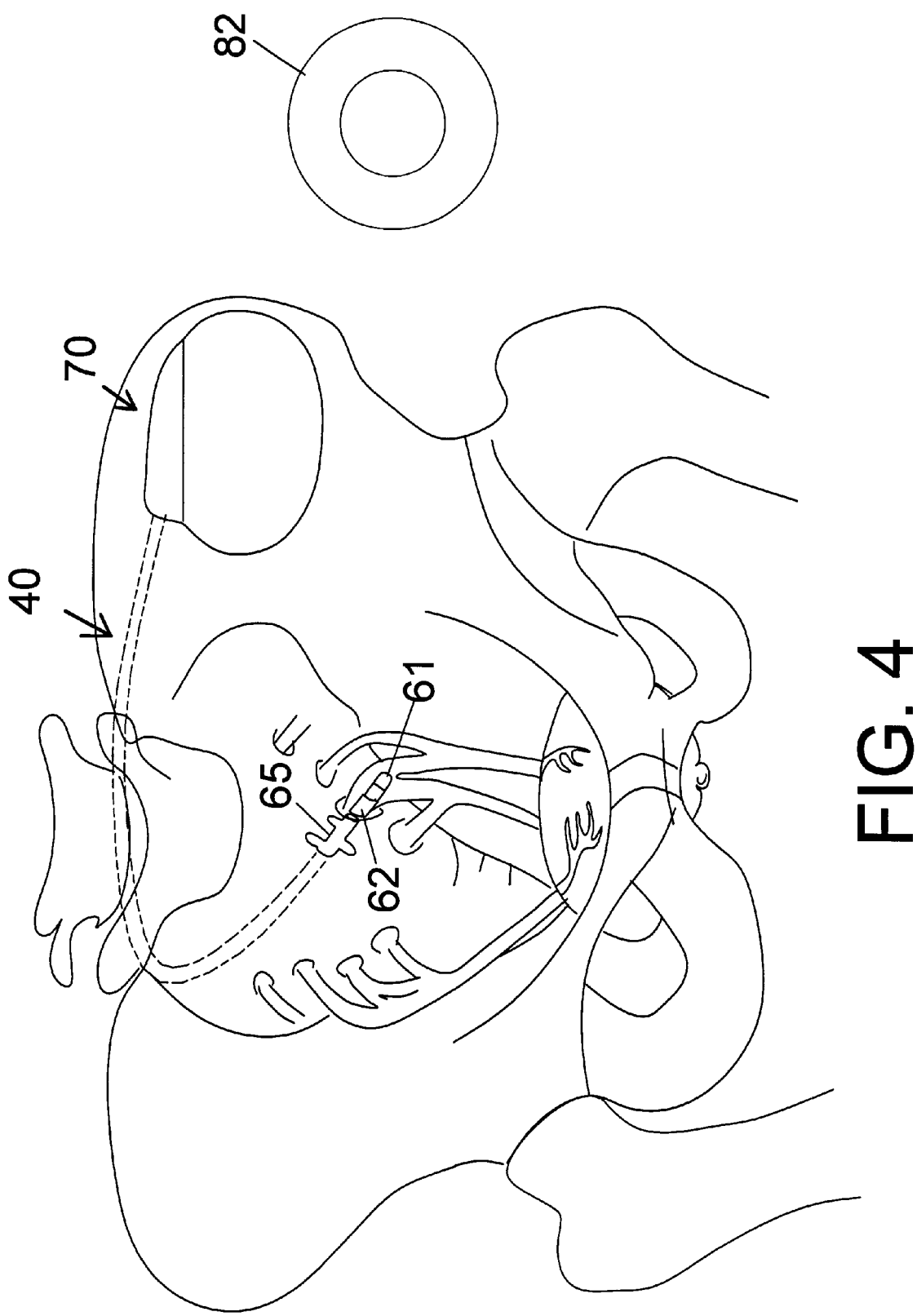
FIG. 4 is a schematic diagram of the sacral region showing electrodes in sacral foraman, and placement of the implantable pulse generator.
Figure 5:
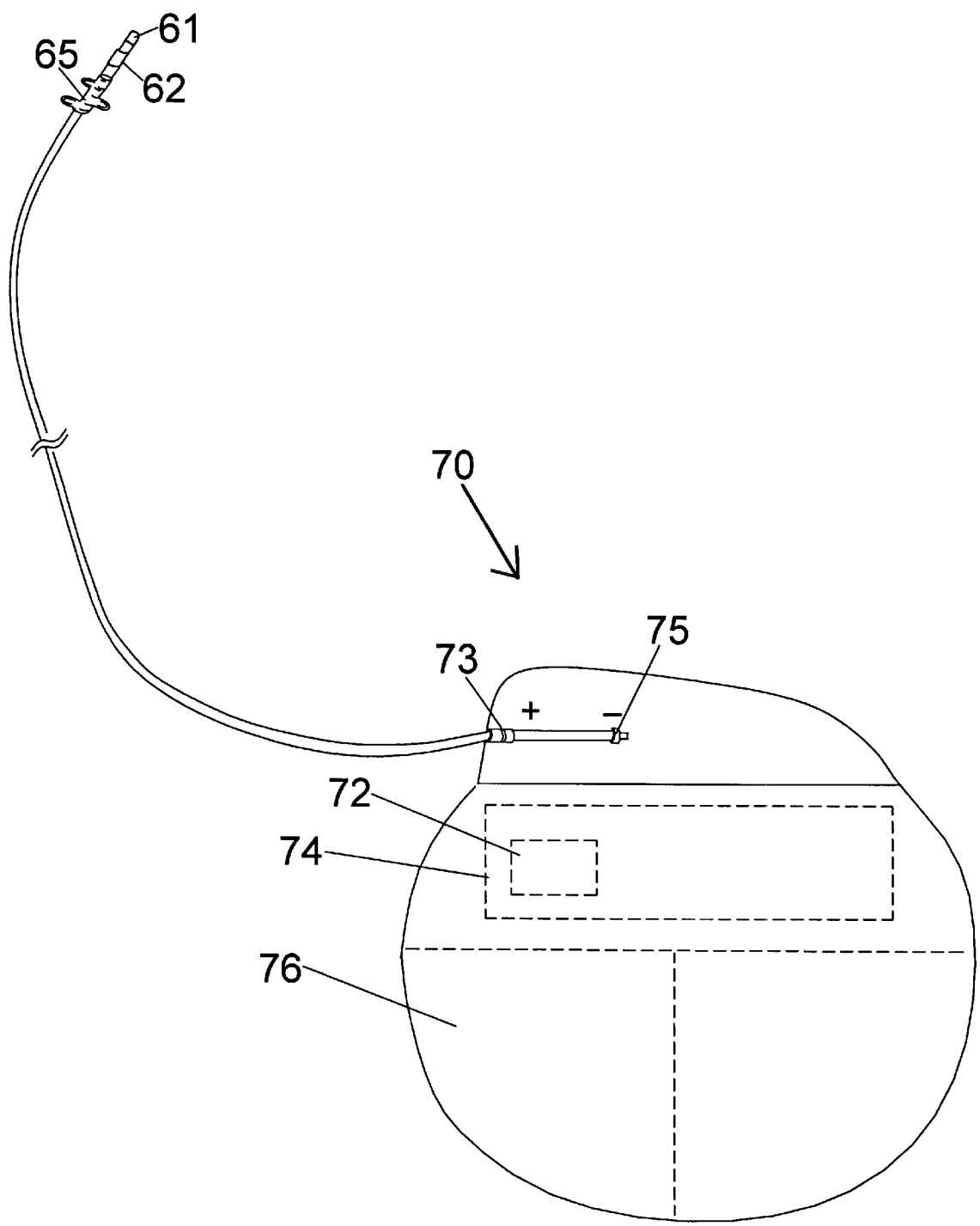
FIG. 5 is a close-up of the implantable neurostimulator system.

FIG. 5 shows the basic elements of the implantable pulse generator (IPG) system, that are well known in the art. The output of the pulse generator 70 is delivered to the sacral plexus of a patient via two electrodes 61,62 in contact with the sacral nerves. The conductors (not shown) connecting the electrodes 61,62 to the pulse generator 70 are insulated from each other and from the body tissues and fluids by material made of either medical grade silicone or polyurethane. The hybrid circuitry 74 containing a microprocessor 72 is driven by Lithium batteries 76, preferably Lithium Thionyl Chloride.

Electronic circuitry 74 and batteries 76 are encased in a titanium can which is punched from titanium sheet. Housing is made of titanium because it is biologically compatible, and the pulse generator case is hermetically sealed utilizing laser welding techniques standard in the art.

Figure 6:
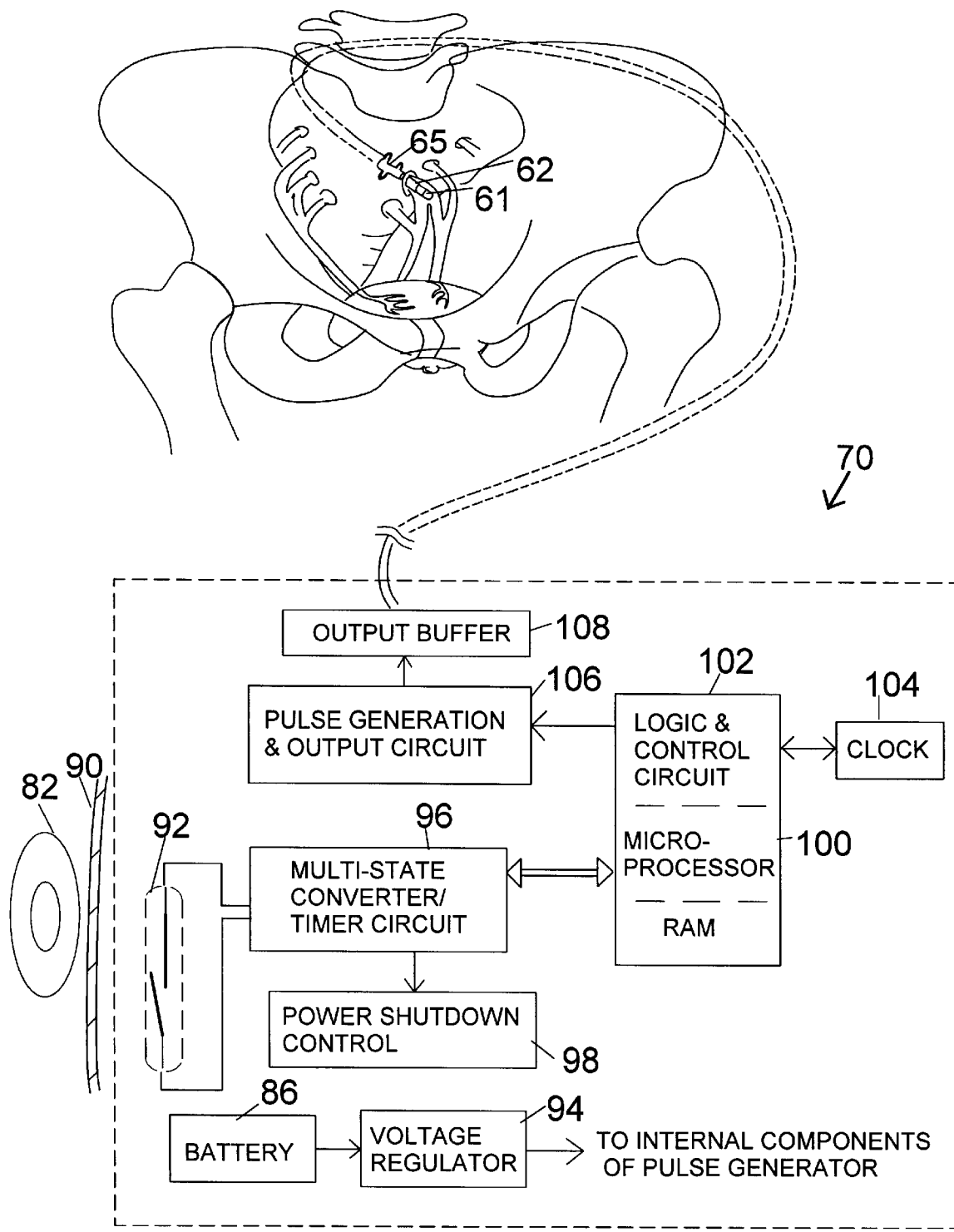
FIG. 6 is a simplified block diagram showing control of the implantable neurostimulator with a magnet.

Referring now to FIG. 6, the implantable pulse generator 70 is provided with a reed switch 92 and memory circuitry. The reed switch 92 being remotely actuable by means of a magnet 82 brought into proximity of the pulse generator 70, in accordance with common practice in the art. In this embodiment, the reed switch 92 is coupled to multi-state converter/timer circuit 96, such that a single short or prolonged closure of the reed switch can be used as a means for non-invasive encoding and programming of the pulse generator 70 parameters.

Figure 7:
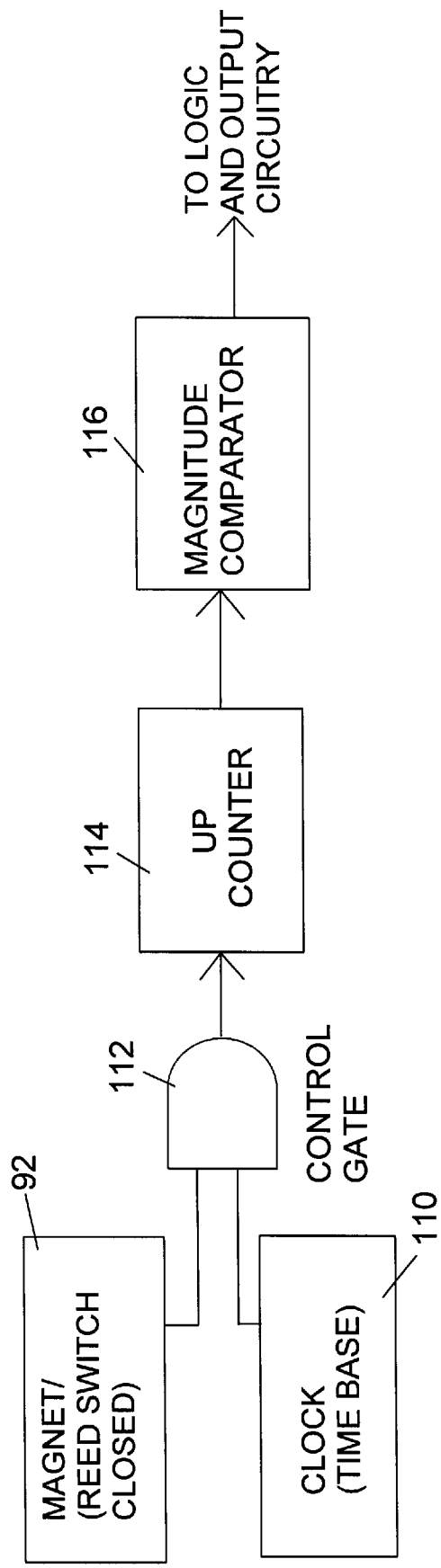
FIG. 7 is a schematic diagram showing implementation of multi-state converter.

The closing of the reed switch 92 triggers a counter. As shown in FIG. 7, the magnet and timer are ANDed together. In the presently preferred embodiment, the system is configured such that during the time that the magnet 82 is held over the pulse generator 70, the output level goes from LOW stimulation state to the next higher stimulation state every 5 seconds. Once the magnet 82 is removed, regardless of the state of stimulation, an application of the magnet, without holding it over the pulse generator 70, triggers the OFF state, which also resets the counter.

Figure 8A:
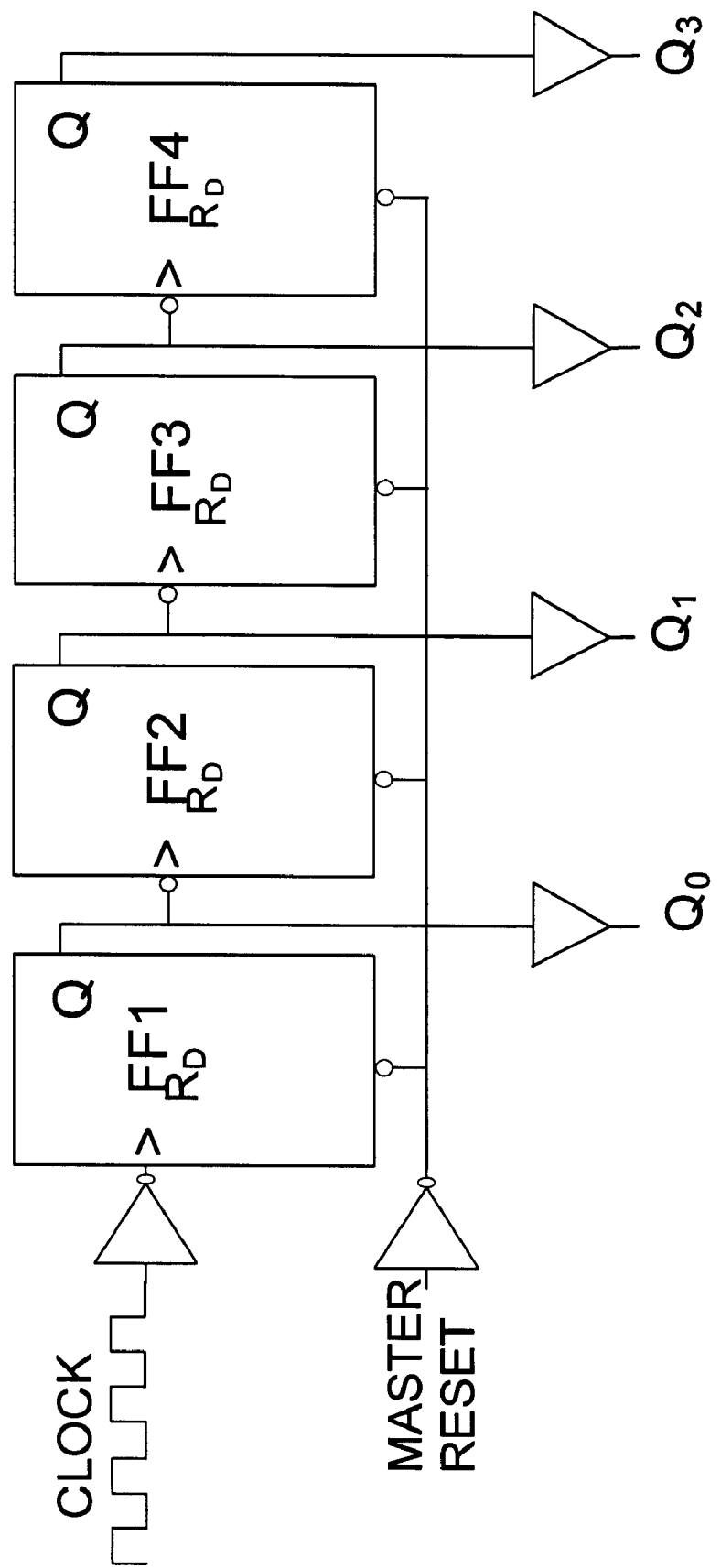
FIG. 8A is a logic diagram of a 4 bit counter.
Figure 8:
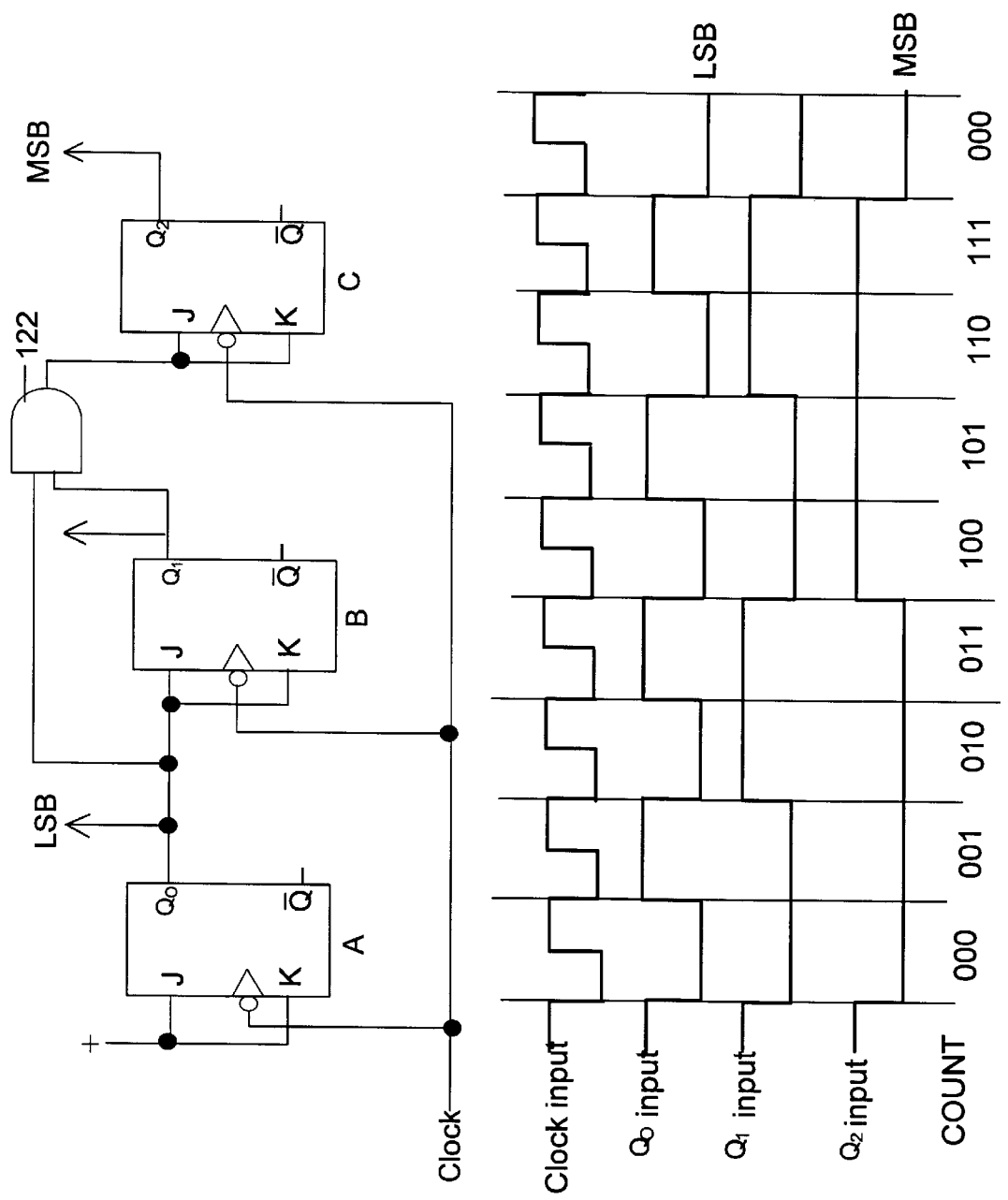
FIG. 8B is a synchronous up-counter with 3 J-K flip flops.

Standard counters of the type shown with logic diagrams in FIGS. 8A and 8B may be used. The example shown in FIG. 8A is of a four bit counter, consisting of four T flip-flops. The example shown in FIG. 8B is of a synchronous up-counter with 3 J-K flip flops, and the bistables are master-slave JKs. The AND gate 122 is there to detect the movement when the output of the first two bistables is at logic 1. This detects a binary count of 11 and sends a signal to switch on the next bistable to give the next count as $100_2$ (base 2). This is also shown in the timing diagram at the bottom half of the figure. These synchronous counters can be easily extended by adding more bistables for a higher count.

Once the prepackaged/predetermined logic state is activated by the logic and control circuit 102, as shown in FIG. 6, the pulse generation and amplification circuit 106 deliver the appropriate electrical pulses to the sacral nerves of the patient via an output buffer 108. Timing signals for the logic and control circuit 102 of the pulse generator 70 are provided by a crystal oscillator 104. The battery 86 of the pulse generator 70 has terminals connected to the input of a voltage regulator 94. The regulator 94 smoothes the battery output and supplies power to the internal components of the pulse generator 70. A microprocessor 100 controls the program parameters of the device, such as the voltage, pulse width, frequency of pulses, on-time and off-time. The microprocessor may be a commercially available, general purpose microprocessor or microcontroller, or may be a custom integrated circuit device augmented by standard RAM/ROM components.

In the presently preferred embodiment, there are four stimulation states. A larger (or smaller) number of states can be achieved using the same methodology, and is considered within the scope of the invention. These four states are, LOW stimulation state, LOW-MED stimulation state, MED stimulation state, and HIGH stimulation state. Examples of stimulation parameters (delivered to the sacral nerves) for each state are as follows, LOW stimulation state example is,
Current output: 2.0 milliAmps.
Pulse width: 0.25 msec.
Pulse frequency: 20 Hz
Cycles: 20 sec. on-time and 2.0 min. off-time in repeating cycles.

LOW-MED stimulation state example is,
Current output: 2.5 milliAmps,
Pulse width: 0.30 msec.
Pulse frequency: 30 Hz
Cycles: 1.5 min. on-time and 20.0 min. off-time in repeating cycles.

MED stimulation state example is,
Current output: 3.5 milliAmps.
Pulse width: 0.30 msec.
Pulse frequency: 40 Hz
Cycles: 2.0 min. on-time and 20.0 min. off-time in repeating cycles.

HIGH stimulation state example is,
Current output: 4.5 milliAmps,
Pulse width: 0.40 msec.
Pulse frequency: 50 Hz
Cycles: 3.0 min. on-time and 20.0 min. off-time in repeating cycles.

These prepackaged/predetermined programs are mearly examples, and the actual stimulation parameters may deviate somewhat from these.

It will be readily apparent to one skilled in the art, that other schemes can be used for the same purpose. For example, instead of placing the magnet 82 on the pulse JAYS generator 70 for a prolonged period of time, different stimulation states can be encoded by the sequence of magnet applications. Accordingly, in an alternative embodiment there can be four logic states, OFF, LOW stimulation (LS) state, MED stimulation state (MS), and HIGH stimulation (HS) state. Each logic state again corresponds to a prepackaged/predetermined program such as presented above. In such an embodiment, the system could be configured such that one application of the magnet triggers the generator into LS State. If the generator is already in the LS state then one application (of the magnet) triggers the device into OFF State. Two successive magnet applications triggers the generator into MED stimulation state, and three successive magnet applications triggers the pulse generator into the HIGH Stimulation State. Subsequently, one application of the magnet while the device is in any stimulation state, triggers the device OFF.

Figure 9:
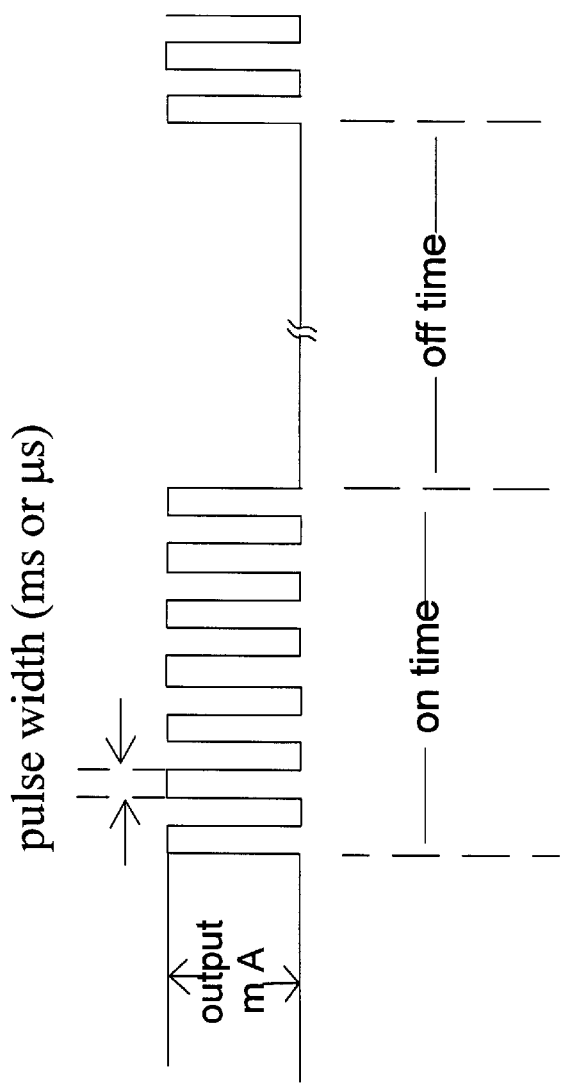
FIG. 9 is a diagram which shows the pulse train transmitted by the implant unit.
Figure 10:
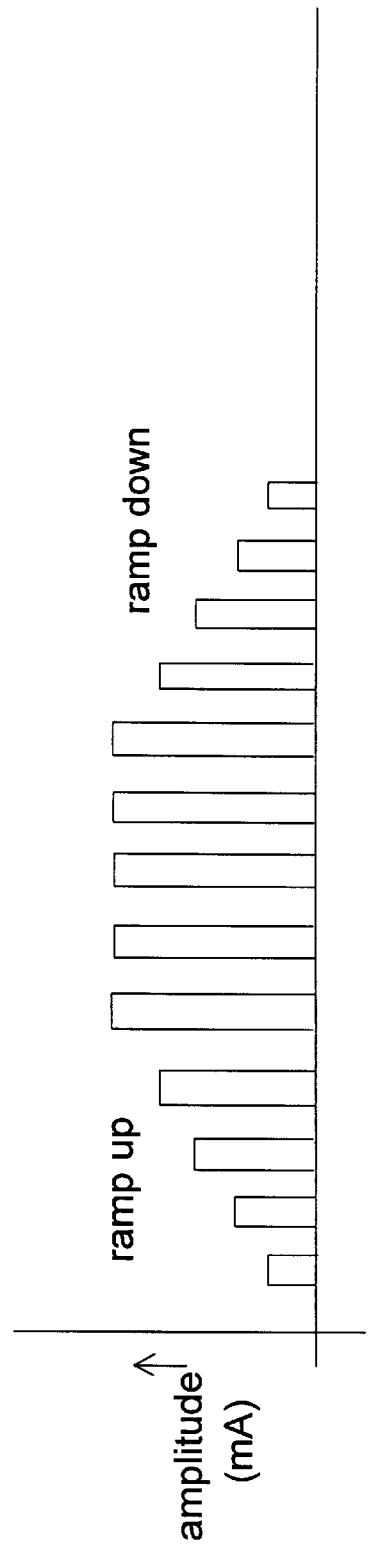
FIG. 10 shows the ramp-up and ramp-down characteristic of the pulse train.

The approximate waveform of pulses delivered to the nerve tissue for stimulation therapy are shown graphically in FIG. 9. As shown in FIG. 10, for patient comfort when the electrical stimulation is turned on, the system is configured to deliver electrical stimulation in ramp up and ramp down fashion, instead of abrupt delivery of electrical pulses.

Figure 11:
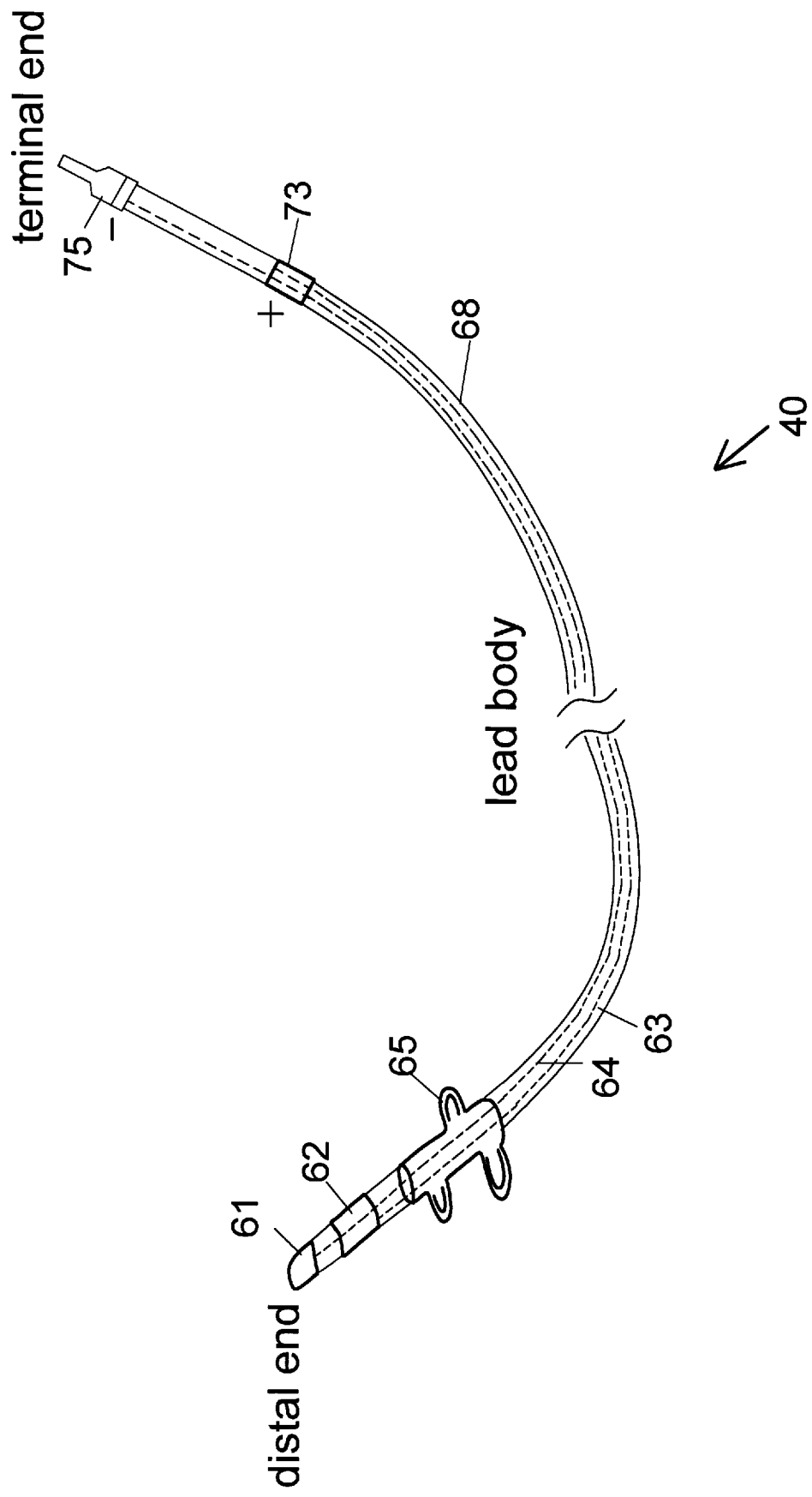
FIG. 11 is a schematic diagram of the implantable lead.

Referring now to FIG. 11, the implanted lead component of the system is similar to cardiac pacemaker leads, except for distal (electrode) portion of the lead 40. The lead terminal may be linear bipolar or bifurcated, and plug(s) into the cavity of the pulse generator 70. The lead body insulation 68 may be constructed of polyurethane, medical grade silicone, or silicone reinforced with polytetrafluoro-ethylene (PTFE). The electrodes for stimulating the sacral nerves may either be cylindrical or oval shaped. These stimulating electrodes may be made of pure platinum, platinum/Iridium alloy or platinum/iridium coated with titanium nitride. The conductor connecting the terminal to the electrodes is made of an alloy of nickel-cobalt. The implanted lead design variables are also summarized in the table below.

Table of lead design variables

| Proximal End | | | | | Distal End |
|---|---|---|---|---|---|
| Lead Terminal | Lead body-Insulation Materials | Lead-Coating | Conductor (connecting proximal and distal ends) | Electrode - Material | Electrode - Type |
| Linear Bipolar | Polyurethane | Anti-microbial coating | Alloy of Nickel-Cobalt | Pure Platinum | Cylindrical electrode |
| Bifurcated | Silicone | Anti-Inflamatory coating | | Platinum-Iridium (Pt/IR) Alloy | Oval electrode |
| | Silicone with Polytetrafluoroethylene (PTFE) | Lubricious coating | | Pt/Ir coated with Titanium Nitride Carbon | Steroid eluting |

Once the lead is fabricated, coating such as anti-microbial, anti-inflammatory, or lubricious coating may be applied to the body of the lead.

What is claimed is:

1. An apparatus for neuromodulation of sacral nerves, comprising:
   a) an implantable lead having at least one electrode adapted to be in contact with sacral nerves and connected to a programmerless pulse generator;
   b) said programmerless pulse generator comprising circuitry, power source, and at least two predetermined programs to control electrical signals;
   c) means to control said at least two predetermined programs by an external magnet,
whereby said implantable pulse generator provides neuromodulation therapy which is controllable by an external magnet.

2. The apparatus of claim 1 wherein said sacral nerves comprises sacral plexus and its branches.

3. The apparatus of claim 1, wherein
   a) said electrical signals comprises at least one variable component selected from the group consisting of the current amplitude, pulse width, frequency, on-time and off-time, and;
   b) said at least two predetermined programs control the variable component of said electrical signals.

4. The apparatus of claim 1, comprises treatment for one of urinary incontinence, neuro-urological disorders, bladder control, bladder inflammation, and bladder pain such as may be caused by Interstitial cystitis disease or the like.

5. A method of treatment for one of urinary incontinence, neurourological disorders, bladder control, bladder inflammation, bladder pain such as may be caused by Interstitial cystitis disease or the like, comprising:
   a) providing a programmerless pulse generator with circuitry, power source, and at least two predetermined programs to control the electrical signals;
   b) providing an implanted lead having at least one electrode in contact with sacral nerves and connected to the pulse generator; and,
   c) providing a means for controlling said at least two predetermined programs by an external magnet;
whereby said implanted pulse generator provides neuromodulation therapy which is controllable by an external magnet.

6. The method of claim 5 wherein said sacral nerves comprises sacral plexus and its branches.

7. The method of claim 5, wherein said electric signals comprises at least one variable component selected from the group consisting of the current amplitude, pulse width, frequency, on-time and off-time.

8. The method of claim 5, wherein said at least two of predetermined programs control the variable component of said electrical signals.

9. A method of neuromodulation of sacral nerves comprising:
   a) providing a programmerless implantable pulse generator comprising circuitry, power source, at least two predetermined programs to control the electrical signals to said sacral nerves;
   b) providing an implantable lead having at least one electrode in contact with said sacral nerves and connected to said pulse generator;
   c) activating selectively one of said at least two predetermined programs;
whereby said implanted pulse generator provides neuromodulation therapy to said sacral nerves.

10. The method of claim 9, wherein said pulse generator comprises means to control said predetermined programs with an external magnet.

11. The method of claim 9, wherein said sacral nerves comprises sacral plexus and its branches.

* * * * *